United States Patent
Adam et al.

(10) Patent No.: US 9,227,885 B2
(45) Date of Patent: *Jan. 5, 2016

(54) PROCESS TO MAKE OLEFINS FROM ISOBUTANOL

(71) Applicant: TOTAL RESEARCH & TECHNOLOGY FELUY, Seneffe (Feluy) (BE)

(72) Inventors: Cindy Adam, Wierde (BE); Delphine Minoux, Nivelles (BE); Nikolai Nesterenko, Nivelles (BE); Sander Van Donk, Sainte-Adresse (FR); Jean-Pierre Dath, Beloeil (BE)

(73) Assignee: TOTAL RESEARCH & TECHNOLOGY FELUY, Seneffe (Feluy) (BE)

( * ) Notice: Subject to any disclaimer, the term of this patent is extended or adjusted under 35 U.S.C. 154(b) by 0 days.

This patent is subject to a terminal disclaimer.

(21) Appl. No.: 14/830,898

(22) Filed: Aug. 20, 2015

(65) Prior Publication Data

US 2015/0353444 A1    Dec. 10, 2015

Related U.S. Application Data

(63) Continuation of application No. 14/692,408, filed on Apr. 21, 2015, which is a continuation of application No. 13/813,115, filed as application No. PCT/EP2011/061582 on Jul. 8, 2011, now Pat. No. 9,056,806.

(30) Foreign Application Priority Data

Aug. 3, 2010 (EP) ..................... 10171669

(51) Int. Cl.
| | |
|---|---|
| *C07C 1/22* | (2006.01) |
| *C07C 1/24* | (2006.01) |
| *C07C 4/06* | (2006.01) |
| *C08F 210/02* | (2006.01) |
| *C08F 210/06* | (2006.01) |

(52) U.S. Cl.
CPC ... *C07C 1/24* (2013.01); *C07C 4/06* (2013.01); *C08F 210/02* (2013.01); *C08F 210/06* (2013.01); *C07C 2529/85* (2013.01)

(58) Field of Classification Search
CPC .............. C07C 1/22; C07C 1/24; C07C 4/06; C07C 6/04
USPC .......................................... 585/638, 639, 640
See application file for complete search history.

(56) References Cited

U.S. PATENT DOCUMENTS 6,797,851 B2 * 9/2004 Martens et al. ........... C07C 1/20
585/639

* cited by examiner

*Primary Examiner* — In Suk Bullock
*Assistant Examiner* — Sharon Pregler

(57) ABSTRACT

A process for the conversion of an alcohol mixture may include introducing into a reactor a stream including the alcohol mixture mixed with a stream including olefins having 4 carbon atoms or more. The process may include contacting the stream with a single catalyst at a temperature above 500° C. in the reactor at conditions effective to dehydrate isobutanol, forming $C_4^+$ olefins, and to catalytically crack the $C_4^+$ olefins. The single catalyst may be an acid catalyst adapted to cause both the dehydration and catalytic cracking. The process may include recovering an effluent including ethylene, propylene, and water, and fractionating the effluent.

25 Claims, No Drawings

PROCESS TO MAKE OLEFINS FROM ISOBUTANOL

CROSS-REFERENCE TO RELATED APPLICATIONS

This application is a Continuation of U.S. patent application Ser. No. 14/692,408, filed on Apr. 21, 2015, which is a Continuation of U.S. patent application Ser. No. 13/813,115, filed on Apr. 5, 2013, now issued as U.S. Pat. No. 9,056,806, which is a National Stage Entry of PCT/EP2011/061582, filed on Jul. 8, 2011, which claims priority from EP 10171669.4, filed on Aug. 3, 2010, the entireties of which are incorporated herein by reference.

FIELD OF THE INVENTION

The present invention relates to the simultaneous dehydration and cracking of isobutanol on a catalyst to produce an olefin stream comprising propylene. The limited supply and increasing cost of crude oil has prompted the search for alternative processes for producing hydrocarbon products such as propylene. i-Butanol can be obtained by fermentation of carbohydrates coming from the biomass, via the syngas route or base-catalysed Guerbet condensation. Made up of organic matter from living organisms, biomass is the world's leading renewable energy source.

BACKGROUND OF THE INVENTION

The bio-ethanol is one of the most relevant sources of bio-carbon today. This platform molecule available today at a price of its calorific value is venturing out of fuel application being used as precursor for base chemicals. While the ethylene can easily produced by dehydration from ethanol, the direct conversion of ethanol to propylene is problematic due to very low yield.

One step process provides a wide diversity in the formed products obtained in minor amounts which monetizing is not very obvious. Multistep process which includes ethanol dehydration to ethylene, offers better overall selectivity to propylene. However, the obtained ethylene has to be first dimerized to butene or oligomerized to be further reacted via metathesis or via cracking in OCP (olefin cracking process) reactor. The complexity of the multistep process increases significantly the manufacturing costs of bio-propylene.

The way to produce bio-propylene can be accomplished by employing a new concept: using isobutanol as a platform molecule. Of the described routes towards isobutanol, the Guerbet condensation, the synthesis gas conversion to alcohols and the 2-keto acid pathway from carbohydrates are routes that can use biomass as primary feedstock. The fermentation of sugar as well as a syn-gas conversion may result directly to formation of heavy alcohols (C3+), in particular i-butanol, which is often an abundant product (Applied Catalysis A, general, 186, p. 407, 1999 and Chemiker Zeitung, 106, p. 249, 1982).

Gasification of biomass results in synthesis gas that can be converted after purification into methanol, ethanol, propanol or directly into isobutanol. In addition, methanol and ethanol or propanol resourced from biomass can be further condensed to isobutanol. The base-catalysed Guerbet condensation of methanol with ethanol and/or propanol increases the concentration of i-butanol in the alcohol fraction and in particular in C3+ heavy alcohols fraction (J. of Molecular Catalysis A: Chemical 200, 137, 2003 and Applied Biochemistry and Biotechnology, 113-116, p. 913, 2004).

Isobutanol (2-methyl-1-propanol) has historically found limited applications and its use resembles that of 1-butanol. It has been used as solvent, diluent, wetting agent, cleaner additive and as additive for inks and polymers. Recently, isobutanol has gained interest as fuel or fuel component as it exhibits a high octane number (Blend Octane R+M/2 is 102-103) and a low vapor pressure (RVP is 3.8-5.2 psi).

Isobutanol is often considered as a byproduct of the industrial production of 1-butanol (Ullmann's encyclopedia of industrial chemistry, $6^{th}$ edition, 2002). It is produced from propylene via hydroformylation in the oxo-process (Rh-based catalyst) or via carbonylation in the Reppe-process (Co-based catalyst). Hydroformylation or carbonylation makes n-butanal and iso-butanal in ratios going from 92/8 to 75/25. To obtain isobutanol, the iso-butanal is hydrogenated over a metal catalyst.

Recently, new biochemical routes have been developed to produce selectively isobutanol from carbohydrates. The new strategy uses the highly active amino acid biosynthetic pathway of microorganisms and diverts its 2-keto acid intermediates for alcohol synthesis. 2-Keto acids are intermediates in amino acid biosynthesis pathways. These metabolites can be converted to aldehydes by 2-keto-acid decarboxylases (KDCs) and then to alcohols by alcohol dehydrogenases (ADHs). Two non-native steps are required to produce alcohols by shunting intermediates from amino acid biosynthesis pathways to alcohol production (Nature, 451, p. 86, 2008 and US patent 2008/0261230). Recombinant microorganisms are required to enhance the flux of carbon towards the synthesis of 2-keto-acids. In the valine biosynthesis 2-ketoisovalerate is an intermediate. Glycolyse of carbohydrates results in pyruvate that is converted into acetolactate by acetolactate synthase. 2,4-dihydroxyisovalerate is formed out of acetolactate, catalysed by isomeroreductase. A dehydratase converts the 2,4-dihydroxyisovalerate into 2-keto-isovalerate. In the next step, a keto acid decarboxylase makes isobutyraldehyde from 2-keto-isovalerate. The last step is the hydrogenation of isobutyraldehyde by a dehydrogenase into isobutanol.

The direct 2-keto acid pathway can produce isobutanol from carbohydrates that are isolated from biomass. Simple carbohydrates can be obtained from plants like sugar cane, sugar beet. More complex carbohydrates can be obtained from plants like maize, wheat and other grain bearing plants. Even more complex carbohydrates can be isolated from substantially any biomass, through unlocking of cellulose and hemicellulose from lignocelluloses.

The isobutanol can be dehydrated to corresponding mixture of olefins containing the same number of atoms. Dehydration of butanols has been described on alumina-type catalysts (Applied Catalysis A, General, 214, p. 251-257, 2001).

Both double-bond shift and skeletal isomerisation has been obtained at very low space velocity (or very long reaction time) corresponding to a GHSV (Gas Hourly Space Velocity=ratio of feed rate (gram/h) to weight of catalyst (ml)) of less than 1 gram·ml$^{-1}$·h$^{-1}$. The dehydration reactions of alcohols to produce alkenes with the same number of carbons have been known for a long time (J. Catal. 7, p. 163, 1967 and J. Am. Chem. Soc. 83, p. 2847, 1961). Many available solid acid catalysts can be used for alcohol dehydration (Stud. Surf. Sci. Catal. 51, p. 260, 1989), the European patent EP0150832, Bulletin of the Chemical Society of Japan, vol 47(2), 424-429 (1974). However, γ-aluminas are the most commonly used, especially for the longer chain alcohols (with three and more carbon atoms). This is because catalysts with stronger acidity, such as the silica-aluminas, molecular sieves, zeolites or resin catalysts can promote double-bond shift, skeletal isomerization and other olefin inter-conversion reactions.

The primary product of the acid-catalysed dehydration of isobutanol is iso-butene and water:

So, the dehydration may result in substantially pure isobutene stream or in blended olefinic stream reach in butenes if a secondary reaction occurs on the catalyst.

The production of light olefins (ethylene and propylene) from a mixed alcohol feedstock in an oxygenates to olefins process has been described in the U.S. Pat. No. 7,288,689. Said patent provides various processes for producing C1 to C4 alcohols, optionally in a mixed alcohol stream, and optionally converting the alcohols to light olefins. In one embodiment, it includes directing a first portion of a syngas stream to a methanol synthesis zone wherein methanol is synthesized. A second portion of the syngas stream is directed to a fuel alcohol synthesis zone wherein fuel alcohol is synthesized. The methanol and at least a portion of the fuel alcohol are directed to an oxygenate to olefin reaction system for conversion thereof to ethylene and propylene. In this prior art "fuel alcohol" means an alcohol-containing composition comprising ethanol, one or more C3 alcohols, one or more C4 alcohols and optionally one or more C5+ alcohols. At col 21 lines 14+ is mentioned " . . . Additionally or alternatively, the fuel alcohol-containing stream comprises one or more C4 alcohols, preferably on the order of from about 0.1 to about 20 weight percent C4 alcohols, preferably from about 1 to about 10 weight percent C4 alcohols, and most preferably from about 2 to about 5 weight percent C4 alcohols, based on the total weight of the fuel alcohol-containing stream. The fuel alcohol-containing stream preferably comprises at least about 5 weight percent C3-C4 alcohols, more preferably at least about 10 weight percent C3-C4 alcohols, and most preferably at least about 15 weight percent C3-C4 alcohols . . . ". Preferably, the molecular sieve catalyst composition comprises a small pore zeolite or a molecular sieve selected from the group consisting of: MeAPSO, SAPO-5, SAPO-8, SAPO-11, SAPO-16, SAPO-17, SAPO-18, SAPO-20, SAPO-031, SAPO-34, SAPO-35, SAPO-36, SAPO-37, SAPO-40, SAPO-41, SAPO-42, SAPO-44, SAPO-47, SAPO-56, AEUCHA intergrowths, metal containing forms thereof, intergrown forms thereof, and mixtures thereof.

EP 2070896 A1 describes the dehydration of 1-butanol on a porous crystalline aluminosilicate (TON type) in the hydrogen form. At 500° C. the products are in wt %:
propylene 10.76
trans-butene-2 16.99
butene-1 13.49
isobutene 31.30
cis-butene-2 13.33

U.S. Pat. No. 6,768,037 describes a process for upgrading a Fischer-Tropsch product comprising paraffins, oxygenates (alcohols), and C6+ olefins. The process includes contacting the Fischer-Tropsch product with an acidic olefin cracking catalyst (ZSM-5) to convert the oxygenates and C6+ olefins to form light olefins. The contacting conditions include a temperature in the range of about 500° F. to 850° F., a pressure below 1000 psig, and a liquid hourly space velocity in the range of from about 1 to 20 hr$^{-1}$. The process further includes recovering the Fischer-Tropsch product comprising unreacted paraffins, and recovering the light olefins. At col 6 lines 16+ is mentioned " . . . The product from a Fischer-Tropsch process contains predominantly paraffins; however, it may also contain $C_{6+}$ olefins, oxygenates, and heteroatom impurities. The most abundant oxygenates in Fischer-Tropsch products are alcohols, and mostly primary linear alcohols. Less abundant types of oxygenates in Fischer-Tropsch products include other alcohol types such as secondary alcohols, acids, esters, aldehydes, and ketones . . . ".

U.S. Pat. No. 4,698,452 relates to a novel process for the conversion of ethanol or its mixtures with light alcohols and optionally water into hydrocarbons with specific and unusual selectivity towards ethylene. More particularly, it relates to the use of ZSM-5 zeolite based catalysts into which Zn alone or Zn and Mn are incorporated. The preferred reaction conditions used in the experiments are as follows: temperature=300° C.-450° C. (most preferred 400° C.); catalyst weight=4 g; total pressure=1 atm; alcohol or aqueous ethanol pressure=0.9 atm; inert gas (stripping gas)=nitrogen; weight hourly space velocity (W.H.S.V.)=2.4 h-1; duration of a run=4 hours. At table 3 dehydration of isobutanol has been made on ZSM-5 (Zn—Mn) and produces paraffins C1-C4, ethylene, propylene, butenes, aromatics and aliphatics.

It has now been discovered that isobutanol or a mixture of isobutanol and other alcohols containing three and more carbon atoms can be simultaneously dehydrated and cracked to propylene in a one-pot reactor to produce propylene rich feedstock.

BRIEF SUMMARY OF THE INVENTION

The present invention relates to a process for the conversion of an alcohols mixture (A) comprising about 20 w % to 100% isobutanol to make essentially propylene, comprising:
a) introducing in a reactor (A) a stream comprising the mixture (A), mixed with a stream (D1) comprising olefins having 4 carbon atoms or more (C4+ olefins), optionally water, optionally an inert component,
b) contacting said stream with a catalyst (A1) at a temperature above 500° C. in said reactor (A) at conditions effective to dehydrate at least a part of the isobutanol and other alcohols, if any, and make a cracking,
c) recovering from said reactor (A) an effluent comprising: ethylene, propylene, water, optionally unconverted alcohols of the mixture (A), various hydrocarbons, and the optional inert component of step a),
d) fractionating said effluent of step c) to produce at least an ethylene stream, a propylene stream, a fraction consisting essentially of hydrocarbons having 4 carbon atoms or more, water and the optional inert component of step a),
optionally recycling ethylene in whole or in part at the inlet of the reactor (A),
optionally recycling the fraction consisting essentially of hydrocarbons having 4 carbon atoms or more at the inlet of the reactor (A).

Advantageously, before recycling said hydrocarbons having 4 carbon atoms or more at the inlet of the reactor (A), said hydrocarbons having 4 carbon atoms or more are sent to a second fractionator to purge the heavies, water and optionally oxygenates.

In an embodiment the alcohol feed is subjected to purification to reduce the content in the metal ions, in more particularly in Na, Fe K, Ca and Al.

In a specific embodiment the alcohol mixture (A) comprises 40 to 100 w % of isobutanol.

In a specific embodiment the alcohol mixture (A) comprises 60 to 100 w % of isobutanol.

In a specific embodiment the alcohol mixture (A) comprises 80 to 100 w % of isobutanol.

In a specific embodiment the alcohol mixture (A) comprises essentially isobutanol.

DETAILED DESCRIPTION OF THE INVENTION

As regards the stream introduced at step a) the inert component is any component provided there is no adverse effect on the catalyst. Because the dehydration is endothermic the inert component can be used to bring energy. By way of examples the inert component is selected among the saturated hydrocarbons having up to 10 carbon atoms, naphtenes, nitrogen and $CO_2$. An example of inert component can be any individual saturated compound, a synthetic mixture of the individual saturated compounds as well as some equilibrated refinery streams like straight naphtha, butanes etc. Advantageously it is a saturated hydrocarbon or a mixture of saturated hydrocarbons having from 3 to 7 carbon atoms, more advantageously having from 4 to 6 carbon atoms and is preferably pentane. The weight proportions of respectively alcohols, water and inert component are, for example, 5-100/0-95/0-95 (the total being 100). The stream comprising the alcohol mixture (A) can be liquid or gaseous.

The isobutanol-containing feed can be produced by the Guerbet condensation, the synthesis gas route and the biochemical routes. The feedstock before feeding to cracking reactor can be subjected to a different upgrading procedure including but non-limiting to purification from the metals, separation/extractions of the individual compounds, alcohols interconversion, partial dehydration to ethers, drying etc. The feedstock is essentially free of light alcohols and hydrocarbons. The weight content of these compounds in the mixture is below 10 wt %.

As regards stream (D1), it may comprise any kind of olefin-containing hydrocarbon stream. (D1) may typically comprise from 10 to 100 wt % olefins and furthermore may be fed undiluted or diluted by a diluent, the diluent optionally including a non-olefinic hydrocarbon. In particular, (D1) may be a hydrocarbon mixture containing normal and branched olefins in the carbon range $C_4$ to $C_{10}$, more preferably in the carbon range $C_4$ to $C_6$, optionally in a mixture with normal and branched paraffin's and/or aromatics in the carbon range $C_4$ to $C_{10}$. Typically, the olefin-containing stream has a boiling point of from around −15 to around 180° C.

In particularly preferred embodiments of the present invention, (D1) comprises $C_4$ mixtures from refineries and steam cracking units. Such steam cracking units crack a wide variety of feedstocks, including ethane, propane, butane, naphtha, gas oil, fuel oil, etc. Most particularly, (D1) may comprise a $C_4$ cut from a fluidized-bed catalytic cracking (FCC) unit in a crude oil refinery which is employed for converting heavy oil into gasoline and lighter products. Typically, such a $C_4$ cut from an FCC unit comprises around 30-70 wt % olefin. Alternatively, (D1) may comprise a $C_4$ cut from a unit within a crude oil refinery for producing methyl tert-butyl ether (MTBE) or ethyl tert-butyl ether (ETBE) which is prepared from methanol or ethanol and isobutene. Again, such a $C_4$ cut from the MTBE/ETBE unit typically comprises around 50 wt % olefin. These $C_4$ cuts are fractionated at the outlet of the respective FCC or MTBE/ETBE unit. (D1) may yet further comprise a $C_4$ cut from a naphtha steam-cracking unit of a petrochemical plant in which naphtha, comprising $C_5$ to $C_9$ species having a boiling point range of from about 15 to 180° C., is steam cracked to produce, inter alia, a $C_4$ cut. Such a $C_4$ cut typically comprises, by weight, 40 to 50% 1,3-butadiene, around 25% isobutylene, around 15% butene (in the form of but-1-ene and/or but-2-ene) and around 10% n-butane and/or isobutane. (D1) may also comprise a $C_4$ cut from a steam cracking unit after butadiene extraction (raffinate 1), or after butadiene hydrogenation.

(D1) may yet further alternatively comprise a hydrogenated butadiene-rich $C_4$ cut, typically containing greater than 50 wt % $C_4$ as an olefin. Alternatively, (D1) could comprise a pure olefin feedstock which has been produced in a petrochemical plant.

(D1) may yet further alternatively comprise light cracked naphtha (LCN) (otherwise known as light catalytic cracked spirit (LCCS)) or a $C_5$ cut from a steam cracker or light cracked naphtha, the light cracked naphtha being fractionated from the effluent of the FCC unit, discussed hereinabove, in a crude oil refinery. Both such feedstocks contain olefins. (D1) may yet further alternatively comprise a medium cracked naphtha from such an FCC unit or visbroken naphtha obtained from a visbreaking unit for treating the residue of a vacuum distillation unit in a crude oil refinery.

Advantageously, the blended stream at the entrance of OCP reactor contains at least 1 wt % of the alcohol mixture (A).

As regards the reactor (A), it can be a fixed bed reactor, a moving bed reactor or a fluidized bed reactor. A typical fluid bed reactor is one of the FCC type used for fluidized-bed catalytic cracking in the oil refinery. A typical moving bed reactor is of the continuous catalytic reforming type. The dehydration may be performed continuously in a fixed bed reactor configuration using a pair of parallel "swing" reactors. The various preferred catalysts of the present invention have been found to exhibit high stability. This enables the dehydration process to be performed continuously in two parallel "swing" reactors wherein when one reactor is operating, the other reactor is undergoing catalyst regeneration. The catalyst of the present invention also can be regenerated several times.

As regards the catalyst (Al) of step b), it can be any acid catalyst capable to cause the simultaneous dehydration and cracking of alcohols under above said conditions. One can cite, molecular sieves, modified zeolites (including P-modified zeolites), a lamellar zeolite such as ITQ-2, metal-aluminophosphates. For example, a known catalyst may be used such as a solid acid catalyst of e.g. a clay mineral such as kaolin, such as Al-MCM41, such as an aluminum phosphate The catalyst is employed under particular reaction conditions whereby the catalytic cracking of the $C_4^+$ olefins readily proceeds. Different reaction pathways can occur on the catalyst. Olefinic catalytic cracking may be understood to comprise a process yielding shorter molecules via bond breakage.

The process conditions are selected in order to provide high selectivity towards propylene or ethylene, as desired, a stable olefin conversion over time, and a stable olefinic product distribution in the effluent. Such objectives are favoured with a low pressure, a high inlet temperature and a short contact time, all of which process parameters are interrelated and provide an overall cumulative effect. The process conditions are selected to disfavour hydrogen transfer reactions leading to the formation of paraffins, aromatics and coke precursors.

According to an embodiment the catalyst (A1) is a crystalline Porous Aluminophosphate containing advantageously at least one 10 and/or 12 members ring into the structure.

The porous crystalline aluminophosphate may be one that is comprised of aluminum and phosphorus that are partly substituted by silicon, boron, Ni, Zn, Mg, Mn such as a porous crystalline metalaluminophosphate. The structure of such crystalline porous aluminophosphates may, for example, be those that are identified by codes for zeolites described above as AEL, AFI, AFO or FAU.

The above porous crystalline aluminophosphate is preferably a porous crystalline silicoaluminophosphate. Specifically, SAPO5, and the like having an AFI structure, SAPO41, and the like having an AFO structure, SAPO11, and the like having an AEL structure, structure or SAPO37, and the like having a FAU structure may be mentioned.

According to another specific embodiment, suitable catalysts for the present process is the silicoaluminophosphate molecular sieves, in particular of the AEL group with typical example the SAPO-11 molecular sieve. The SAPO-11 molecular sieve is based on the ALPO-11, having essentially an Al/P ratio of 1 atom/atom. During the synthesis silicon precursor is added and insertion of silicon in the ALPO framework results in an acid site at the surface of the micropores of the 10-membered ring sieve. The silicon content ranges from 0.1 to 10 atom % (Al+P+Si is 100).

Various commercial zeolite products nay be used, or it is possible to use zeolites that have been synthesized by a known method disclosed in e.g. "Verified Synthesis of Zeolitic Materials" ($2^{nd}$ Revised Edition 2001 Elsevier) published by the above IZA.

According to an embodiment the catalyst (A1) is a crystalline silicate containing advantageously at least one 10 members ring into the structure. It is by way of example of the MFI (ZSM-5, silicalite-1, boralite C, TS-1), MEL (ZSM-11, silicalite-2, boralite D, TS-2, SSZ-46), FER (Ferrierite, FU-9, ZSM-35), MTT (ZSM-23), MWW (MCM-22, PSH-3, ITQ-1, MCM-49), TON (ZSM-22, Theta-1, NU-10), ELK) (ZSM-50, EU-1), MFS (ZSM-57), CON (CIT-1) and ZSM-48 family of microporous materials consisting of silicon, aluminium, oxygen and optionally boron. Advantageously in said first embodiment the catalyst (A1) is a crystalline silicate, metal containing crystalline silicate or a dealuminated crystalline silicate.

The crystalline silicate can have a ratio Si/Al of at least about 100 and is advantageously selected among the MFI and the MEL and modified with the metals Mg, Ca, La, Ni, Ce, Zn, Co, Ag, Fe, Cu. The metal content is at least 0.1 wt %.

The dealuminated crystalline silicate is advantageously such as about 10% by weight of the aluminium is removed. Such dealumination is advantageously made by a steaming optionally followed by a leaching.

In another specific embodiment the crystalline silicate catalyst is mixed with a binder, preferably an inorganic binder, and shaped to a desired shape, e.g. pellets. The binder is selected so as to be resistant to the temperature and other conditions employed in the dehydration process of the invention. The binder is an inorganic material selected from clays, silica, metal silicate, metal borates, metal oxides such as $ZrO_2$ and/or metals, or gels including mixtures of silica and metal oxides.

According to an embodiment the catalyst (A1) is a P-modified zeolite (Phosphorus-modified zeolite). Said phosphorus modified molecular sieves can be prepared based on MFI, MOR, MEL, clinoptilolite or FER, MVVW, TON, EUO, MFS and ZSM-48 family of microporous molecular sieves having an initial Si/Al ratio advantageously between 4 and 500. The P-modified zeolites of this recipe can be obtained based on cheap crystalline silicates with low Si/Al ratio (below 30).

By way of example said P-modified zeolite is made by a process comprising in that order:

selecting a zeolite (advantageously with Si/Al ratio between 4 and 500) among $H^+$ or $NH_4^+$-form of MFI, MEL, FER, MOR, clinoptilolite, MWW, TON, EUO, MFS and ZSM-48;
introducing P at conditions effective to introduce advantageously at least 0.05 wt % of P;
separation of the solid from the liquid if any;
an optional washing step or an optional drying step or an optional drying step followed by a washing step;
a calcination step.

The zeolite with low Si/Al ratio has been made previously with or without direct addition of an organic template.

Optionally the process to make said P-modified zeolite comprises the steps of steaming and leaching. The method consists in steaming followed by leaching. It is generally known by the persons in the art that steam treatment of zeolites, results in aluminium that leaves the zeolite framework and resides as aluminiumoxides in and outside the pores of the zeolite. This transformation is known as dealumination of zeolites and this term will be used throughout the text. The treatment of the steamed zeolite with an acid solution results in dissolution of the extra-framework aluminiumoxides. This transformation is known as leaching and this term will be used throughout the text. Then the zeolite is separated, advantageously by filtration, and optionally washed. A drying step can be envisaged between filtering and washing steps. The solution after the washing can be either separated, by way of example, by filtering from the solid or evaporated.

P can be introduced by any means or, by way of example, according to the recipe described in U.S. Pat. No. 3,911,041, U.S. Pat. No. 5,573,990 and U.S. Pat. No. 6,797,851.

The catalyst made of a P-modified zeolite can be the P-modified zeolite itself or it can be the P-modified zeolite formulated into a catalyst by combining with other materials that provide additional hardness or catalytic activity to the finished catalyst product. Advantageously, at least a part of phosphorous is introduced into zeolite before shaping. In a specific embodiment, the formed P-precursor can be further modified with the metals selected from Mg, Ca, La, Ni, Ce, Zn, Co, Ag, Fe, Cu according to the recipe described in WO 09092779 and WO 09092781.

The separation of the liquid from the solid is advantageously made by filtering at a temperature between 0-90° C., centrifugation at a temperature between 0-90° C., evaporation or equivalent.

Optionally, the zeolite can be dried after separation before washing. Advantageously said drying is made at a temperature between 40-600° C., advantageously for 1-10 h. This drying can be processed either in a static condition or in a gas flow. Air, nitrogen or any inert gases can be used.

The washing step can be performed either during the filtering (separation step) with a portion of cold (<40° C.) or hot water (>40 but <90° C.) or the solid can be subjected to a water solution (1 kg of solid/4 liters water solution) and treated under reflux conditions for 0.5-10 h followed by evaporation or filtering.

Final equilibration step is performed advantageously at the temperature 400-800° C. in presence of steam for 0.01-48 h. Advantageously the steam partial pressure is at least 0.1 bars. Air, nitrogen or any inert gases can be fed together with steam. According to a specific embodiment the phosphorous modified zeolite is made by a process comprising in that order:

selecting a zeolite (advantageously with Si/Al ratio between 4 and 500, from 4 to 30 in a specific embodiment) among $H^+$ or $NH_4^+$-form of MFI, MEL, FER, MOR, clinoptilolite, MWW, TON, EUO, MFS and ZSM-48;

steaming at a temperature ranging from 400 to 870° C. for 0.01-200 h;

leaching with an aqueous acid solution at conditions effective to remove a substantial part of Al from the zeolite;

introducing P with an aqueous solution containing the source of P at conditions effective to introduce advantageously at least 0.05 wt % of P;

separation of the solid from the liquid;

an optional washing step or an optional drying step or an optional drying step followed by a washing step;

a calcination step.

Optionally between the steaming step and the leaching step there is an intermediate step such as, by way of example, contact with silica powder and drying.

Optionally the leaching and introducing P are made simultaneously by using an acid mixture comprising phosphorus to make the leaching.

Advantageously the selected MFI, MEL, FER, MOR, clinoptilolite, MWW, TON, EUO, MFS and ZSM-48 (or $H^+$ or $NH_4^+$-form MFI, MEL, FER, MOR, clinoptilolite, MWW, TON, EUO, MFS and ZSM-48) has an initial atomic ratio Si/Al of 100 or lower and from 4 to 30 in a specific embodiment. The conversion to the $H^+$ or $NH_4^+$-form is known per se and is described in U.S. Pat. No. 3,911,041 and U.S. Pat. No. 5,573,990.

Advantageously the final P-content is at least 0.05 wt % and preferably between 0.3 and 7 w %. Advantageously at least 10% of Al, in respect to parent zeolite MFI, MEL, FER, MOR and clinoptilolite, MWW, TON, EUO, MFS and ZSM-48, have been extracted and removed from the zeolite by the leaching.

Then the zeolite either is separated from the washing solution or is dried without separation from the washing solution. Said separation is advantageously made by filtration. Then the zeolite is calcined, by way of example, at 400° C. for 2-10 hours.

In the steam treatment step, the temperature is preferably from 420 to 870° C., more preferably from 480 to 760° C. The pressure is preferably atmospheric pressure and the water partial pressure may range from 13 to 100 kPa. The steam atmosphere preferably contains from 5 to 100 vol % steam with from 0 to 95 vol % of an inert gas, preferably nitrogen. The steam treatment is preferably carried out for a period of from 0.01 to 200 hours, advantageously from 0.05 to 200 hours, more preferably from 0.05 to 50 hours. The steam treatment tends to reduce the amount of tetrahedral aluminium in the crystalline silicate framework by forming alumina.

The leaching can be made with an organic acid such as citric acid, formic acid, oxalic acid, tartaric acid, malonic acid, succinic acid, glutaric acid, adipic acid, maleic acid, phthalic acid, isophthalic acid, fumaric acid, nitrilotriacetic acid, hydroxyethylenediaminetriacetic acid, ethylenediaminetetracetic acid, trichloroacetic acid trifluoroacetic acid or a salt of such an acid (e.g. the sodium salt) or a mixture of two or more of such acids or salts. The other inorganic acids may comprise an inorganic acid such as nitric acid, hydrochloric acid, methansulfuric acid, phosphoric acid, phosphonic acid, sulfuric acid or a salt of such an acid (e.g. the sodium or ammonium salts) or a mixture of two or more of such acids or salts.

The residual P-content is adjusted by P-concentration in the aqueous acid solution containing the source of P, drying conditions and a washing procedure if any. A drying step can be envisaged between filtering and washing steps.

Said P-modified zeolite can be used as itself as a catalyst. In another embodiment it can be formulated into a catalyst by combining with other materials that provide additional hardness or catalytic activity to the finished catalyst product. Materials which can be blended with the P-modified zeolite can be various inert or catalytically active materials, or various binder materials. These materials include compositions such as kaolin and other clays, various forms of rare earth metals, phosphates, alumina or alumina sol, titania, zirconia, quartz, silica or silica sol, and mixtures thereof. These components are effective in densifying the catalyst and increasing the strength of the formulated catalyst. The catalyst may be formulated into pellets, spheres, extruded into other shapes, or formed into a spray-dried particles. The amount of P-modified zeolite which is contained in the final catalyst product ranges from 10 to 90 weight percent of the total catalyst, preferably 20 to 70 weight percent of the total catalyst.

Final equilibration step is performed advantageously at the temperature 400-800° C. in presence of steam for 0.01-48 h. Advantageously the steam partial pressure is at least 0.1 bars. Air, nitrogen or any inert gases can be fed together with steam.

A catalyst has already been described in WO2009098262.

As regards the pressure in steps a) and b), the use of a low alcohol partial pressure which leads to a low olefin partial pressure, for example atmospheric pressure, tends to lower the incidence of hydrogen transfer reactions in the cracking process, which in turn reduces the potential for coke formation which tends to reduce catalyst stability. the partial pressure of the alcohols is advantageously lower than 4 bars absolute (0.4 MPa) and more advantageously from 0.5 to 4 bars absolute (0.05 MPa to 0.4 MPa), preferably lower than 3.5 bars absolute (0.35 MPa) and more preferably lower than 2 bars absolute (0.2 MPa). The pressure of the reactor of step b) can be any pressure but it is more economical to operate at moderate pressure. By way of example the pressure of the reactor ranges from 1 to 30 bars absolute (0.1 MPa to 3 MPa), advantageously from 1 to 20 bars absolute (0.1 MPa to 2 MPa).

As regards the temperature in step b), the reaction is preferably performed at an inlet temperature of the feedstock of from 500° to 650° C., more preferably from 520° to 600° C., yet more preferably from 540° C. to 590° C.

As regards the WHSV of alcohols and optional olefins of D1 in step b), it ranges advantageously from 0.1 to 50 h-1, more advantageously from 1 to 20 h-1, preferably from 5 to 20 h-1, and more preferably from 5 to 15 h-1.

In order to maximize the amount of ethylene and propylene and to minimize the production of methane, aromatics and coke, it is desired to minimize the presence of diolefins in the feed. Diolefin conversion to monoolefin hydrocarbons may be accomplished with a conventional selective hydrogenation process such as disclosed in U.S. Pat. No. 4,695,560 hereby incorporated by reference.

As regards step d), the fractionation of said effluent of step c) said fractionation is carried out by any means, they are known per se.

One skilled in the art will also appreciate that the olefin products made by the present invention can be polymerized, optionally with comonomers, to form polyolefins, particularly polyethylenes and polypropylenes.

EXAMPLES

Experimental

The stainless-steel reactor tube has an internal diameter of 10 mm. 10 ml of catalyst, as pellets of 35-45 mesh, is loaded in the tubular reactor. The void spaces before and after the catalyst are filled with SiC granulates of 2 mm. The temperature profile is monitored with the aid of a thermocouple well placed inside the reactor. The reactor temperature is increased at a rate of 60° C./h to 550° C. under air, kept 2 hours at 550° C. and then purged by nitrogen. The nitrogen is then replaced by the feed at the indicated operating conditions.

The catalytic tests are performed down-flow, with a pressure of about 1.5 bara, with a temperature of about 575° C. and with a weight hour space velocity (WHSV) of about 7 $h^{-1}$.

Analysis of the products is performed by using an on-line gas chromatography.

Example 1

The catalyst is a phosphorous modified zeolite (P-ZSM5), prepared according to the following recipe. A sample of zeolite ZSM-5 (Si/Al=13) in H-form was steamed at 550° C. for 6 h in 100% $H_2O$. Then, 1270 g of the steamed solid was subjected to a contact with 241.3 g of an aqueous solution of $H_3PO_4$ (85% wt) for 2 h under reflux condition (4 ml/1 g zeolite) followed by addition of 69.9 g of CaCO3. Then the solution was dried by evaporation under rigours stirring for 3 days at 80° C. 750 g of the dried sample was extruded with 401.5 g of silica sol Bindzil (34 wt % SiO2), and 3 wt % of extrusion additives. The shaped sample contained about 80 wt % zeolite. The extruded solid was dried at 110° C. for 16 h and steamed at 600° C. for 2 h. The isobutanol co-feeding in the C4 ex-FCC feed has been tested with several mixtures isobutanol/C4 ex-FCC: 80/20, 50/50 and 0/100 wt %. The temperature, pressure and WHSV (reported to isobutanol) have been maintained constant: 1.5 bara, $T_{in}$- 575° C. and an isobutanol space velocity of about 7 $h^{-1}$. For the mixture isobutanol/C4 ex-FCC 100/0, the isobutanol is diluted with water in the ratio 95/5 wt %.

For the selectivity calculation reported to olefins content in the feed, the following assumptions have been done:
  The C4 ex-FCC feed contains 61.3 wt % of non-cyclic olefins and 37.5 wt % of paraffin's.
  The proportion of isobutanol in the feed is assimilated to olefins (CH2-basis).

The table 1 provides the average catalyst performance for 40 hours-on-stream given on CH2-basis and coke free basis.

TABLE 1

| FEED | C4/i-BuOH 80/20 | C4/i-BuOH 50/50 | C4 ex-FCC |
|---|---|---|---|
| P (bara) | 1.5 | 1.5 | 1.5 |
| T (° C.) | 575 | 575 | 575 |
| WHSV (H-1) | 7.1 | 7.1 | 6.8 |
| Conversion (% wt CH2) | 100 | 100 | 100 |
| C2= | 12.0 | 10.0 | 7.7 |
| C3= | 32.8 | 33.1 | 33.0 |

The examples illustrate substantially complete conversion of isobutanol. The propylene selectivity reported on olefins basis in the co-feeding experiments is close to the value which is typically observed for cracking of conventional olefin-containing feedstocks like C4 FCC etc.

The invention claimed is:

1. A process for the conversion of an alcohols mixture comprising about 20 to 100 weight percent isobutanol to make essentially propylene, comprising:
  a) introducing in a reactor a stream comprising the alcohols mixture, mixed with a stream comprising olefins having 4 carbon atoms or more ($C_4^+$ olefins), optionally water, optionally an inert component,
  b) contacting said stream with a single catalyst at a temperature above 500° C. in said reactor at conditions effective to dehydrate at least a part of the isobutanol and other alcohols, if any, forming $C_4^+$ olefins and catalytically crack the $C_4^+$ olefins wherein the single catalyst is an acid catalyst adapted to cause both the dehydration and the catalytic cracking,
  c) recovering from said reactor an effluent comprising: ethylene, propylene, water, optionally unconverted alcohols of the alcohols mixture, various hydrocarbons, and optionally the optional inert component of step a),
  d) fractionating said effluent of step c) to produce at least an ethylene stream, a propylene stream, a fraction consisting essentially of hydrocarbons having 4 carbon atoms or more, water and optionally the optional inert component of step a), optionally recycling ethylene in whole or in part at an inlet of the reactor, optionally recycling the fraction consisting essentially of hydrocarbons having 4 carbon atoms or more at the inlet of the reactor.

2. The process according to claim 1, wherein, before recycling said hydrocarbons having 4 carbon atoms or more at the inlet of the reactor, said hydrocarbons having 4 carbon atoms or more are sent to a second fractionator to purge the heavies.

3. The process according to claim 1, wherein the alcohol mixture is subjected to purification to reduce a content of metal ions selected from Na, Fe, K, Ca and Al in the alcohol mixture.

4. The process according to claim 1, wherein the temperature in the reactor of step a) and b) is up to 650° C.

5. The process according to claim 1, wherein the temperature in the reactor of step a) and b) ranges from 520° C. to 600° C.

6. The process according to claim 1, wherein the temperature in the reactor of step a) and b) ranges from 540° C. to 590° C.

7. The process according to claim 1, wherein the alcohol mixture comprises 40 to 100 weight percent of isobutanol.

8. The process according to claim 1, wherein the alcohol mixture comprises 60 to 100 weight percent of isobutanol.

9. The process according to claim 1, wherein the alcohol mixture comprises 80 to 100 weight percent of isobutanol.

10. The process according to claim 1, wherein the alcohol mixture comprises essentially isobutanol.

11. The process according to claim 1, further comprising fermenting carbohydrates coming from biomass, or from the syngas route or from the base-catalysed Guerbet condensation to obtain the isobutanol.

12. The process according to claim 1, further comprising producing the isobutanol by the direct 2-keto acid pathway from carbohydrates that are isolated from biomass.

13. The process according to claim 1, wherein ethylene is further polymerized optionally with one or more comonomers.

14. The process according to claim 1, wherein propylene is further polymerized optionally with one or more comonomers.

15. The process according to claim 1, wherein the stream comprising olefins having 4 carbon atoms or more ($C_4^+$ olefins) comprises from 10 to 100 weight percent olefins.

16. The process according to claim 1, wherein the stream comprising olefins having 4 carbon atoms or more ($C_4^+$ olefins) comprises a hydrocarbon mixture containing normal and branched $C_4$-$C_{10}$ olefins, optionally in a mixture with normal and branched paraffins, $C_4$-$C_{10}$ aromatics, or combinations thereof.

17. The process according to claim 1, wherein the mixture of the stream comprising olefins having 4 carbon atoms or more ($C_4^+$ olefins) and the alcohol mixture contains at least 1 weight percent of the alcohol mixture at the inlet of the reactor.

18. The process according to claim 1, wherein the single catalyst is a crystalline silicate containing at least one 10 member ring in the structure thereof.

19. The process according to claim 18, wherein the single catalyst is selected from the group consisting of MFI, MEL, FER, MTT, MWW, TON, EUO, MFS, CON and ZSM-48.

20. The process according to claim 18, wherein the single catalyst is selected from the group consisting of ZSM-5, silicalite-1, boralite C, TS-1, ZSM-11, silicalite-2, boralite D, TS-2, SSZ-46, ferrierite, FU-9, ZSM-35, ZSM-23, MCM-22, PSH-3, ITQ-1, MCM-49, ZSM-22, Theta-1, NU-10, ZSM-50, EU-1, ZSM-57, CIT-1 and ZSM-48.

21. The process according to claim 18, wherein the crystalline silicate has a ratio Si/Al of at least 100.

22. The process according to claim 21, wherein the crystalline silicate is an MFI or MEL and is modified with at least 0.1 weight percent of a metal that is Mg, Ca, La, Ni, Ce, Zn, Co, Ag, Fe, or Cu.

23. The process according to claim 18, wherein the crystalline silicate is a dealuminated crystalline silicate.

24. The process according to claim 18, wherein the crystalline silicate is mixed with a binder.

25. The process according to claim 18, wherein the binder is selected from clays, silica, metal silicate, metal borates, metal oxides, and gels including mixtures of silica and metal oxides.

\* \* \* \* \*